(12) United States Patent
Stringham et al.

(10) Patent No.: US 9,946,842 B1
(45) Date of Patent: Apr. 17, 2018

(54) METHODS AND SYSTEMS FOR ROUTING PATIENT INFORMATION TO A COMMUNICATION SERVICE PROVIDER AND TO A COMMUNICATION DEVICE FOR HEARING-IMPAIRED USERS

(71) Applicant: Sorenson IP Holdings, LLC, Salt Lake City, UT (US)

(72) Inventors: Thomas Stringham, Salt Lake City, UT (US); Cameron Tingey, Kaysville, UT (US); James Rollins, Lehi, UT (US); Merle L. Walker, Sandy, UT (US); Shane Roylance, Farmington, UT (US); Michael Sorokine, Bountiful, UT (US); Kenneth Boehme, South Jordan, UT (US)

(73) Assignee: Sorenson IP Holdings, LLC, Salt Lake City, UT (US)

( * ) Notice: Subject to any disclaimer, the term of this patent is extended or adjusted under 35 U.S.C. 154(b) by 2 days.

(21) Appl. No.: 14/717,941

(22) Filed: May 20, 2015

Related U.S. Application Data

(60) Provisional application No. 62/127,227, filed on Mar. 2, 2015.

(51) Int. Cl.
*G06F 19/00* (2011.01)
*H04M 3/42* (2006.01)
*G06Q 50/24* (2012.01)

(52) U.S. Cl.
CPC ........ *G06F 19/3418* (2013.01); *G06F 19/322* (2013.01); *G06Q 50/24* (2013.01); *H04M 3/42391* (2013.01)

(58) Field of Classification Search
CPC ......... A61B 5/121; A61B 5/128; G06F 17/24; G06F 17/273; G06F 17/2765; G09B 21/009; G10L 15/26; G10L 15/265; H04L 12/66; H04M 3/42391; H04M 3/51; H04R 25/505; H04R 25/554; H04R 25/558; H04R 25/70; H04R 25/75; H04R 2225/55

(Continued)

(56) References Cited

U.S. PATENT DOCUMENTS

| 5,909,482 | A | 6/1999 | Engelke |
| 5,974,116 | A | 10/1999 | Engelke et al. |

(Continued)

OTHER PUBLICATIONS

Sycle Noah 4, http://www.audiologyonline.com/interviews/new-sycle-noah-4-synchronizer-12276, Nov. 4, 2014.

(Continued)

*Primary Examiner* — Duc Nguyen
*Assistant Examiner* — Alexander Eljaiek
(74) *Attorney, Agent, or Firm* — Maschoff Brennan

(57) ABSTRACT

Systems, devices, and methods are disclosed for establishing a communication channel between a computer device associated with a hearing-care professional and various devices associated with a communication service provider for providing services to hearing-impaired users. The computer device associated with the hearing-care professional may be configured to generate at least one of a professional certification form and audiogram data through its associated software tools to the various devices associated with the communication service provider.

4 Claims, 9 Drawing Sheets

(58) Field of Classification Search
USPC ........ 379/52, 102.01; 381/58, 60, 73.1, 312; 434/112; 600/25, 559; 704/2, 235
See application file for complete search history.

(56) References Cited

U.S. PATENT DOCUMENTS

| | | | |
|---|---|---|---|
| 5,978,654 | A | 11/1999 | Colwell et al. |
| 6,075,841 | A | 6/2000 | Engelke et al. |
| 6,075,842 | A | 6/2000 | Engelke et al. |
| 6,233,314 | B1 | 5/2001 | Engelke |
| 6,307,921 | B1 | 10/2001 | Engelke et al. |
| 6,493,426 | B2 | 12/2002 | Engelke et al. |
| 6,504,910 | B1 | 1/2003 | Engelke et al. |
| 6,510,206 | B2 | 1/2003 | Engelke et al. |
| 6,549,611 | B2 | 4/2003 | Engelke et al. |
| 6,567,503 | B2 | 5/2003 | Engelke et al. |
| 6,594,346 | B2 | 7/2003 | Engelke |
| 6,603,835 | B2 | 8/2003 | Engelke et al. |
| 6,748,053 | B2 | 6/2004 | Engelke et al. |
| 6,882,707 | B2 | 4/2005 | Engelke et al. |
| 6,885,731 | B2 | 4/2005 | Engelke et al. |
| 6,934,366 | B2 | 8/2005 | Engelke et al. |
| 7,003,082 | B2 | 2/2006 | Engelke et al. |
| 7,006,604 | B2 | 2/2006 | Engelke |
| 7,164,753 | B2 | 1/2007 | Engelke et al. |
| 7,319,740 | B2 | 1/2008 | Engelke et al. |
| 7,555,104 | B2 | 6/2009 | Engelke |
| 7,660,398 | B2 | 2/2010 | Engelke et al. |
| 7,680,465 | B2 | 3/2010 | Zad-Issa |
| 7,881,441 | B2 | 2/2011 | Engelke et al. |
| 8,213,578 | B2 | 7/2012 | Engleke et al. |
| 8,379,801 | B2 | 2/2013 | Romriell et al. |
| 8,416,925 | B2 | 4/2013 | Engelke et al. |
| 8,855,324 | B2 | 10/2014 | Franck |
| 8,908,838 | B2 | 12/2014 | Engelke et al. |
| 8,917,821 | B2 | 12/2014 | Engelke et al. |
| 8,917,822 | B2 | 12/2014 | Engelke et al. |
| 2005/0232169 | A1* | 10/2005 | McLaughlin ..... H04M 3/42391 370/261 |
| 2008/0187108 | A1 | 8/2008 | Engelke et al. |
| 2011/0170672 | A1 | 7/2011 | Engelke et al. |
| 2011/0257994 | A1* | 10/2011 | Givens ................ G06F 19/3418 705/2 |
| 2012/0250837 | A1 | 10/2012 | Engleke et al. |
| 2015/0003635 | A1* | 1/2015 | Baker ................ G06F 19/3487 381/104 |

OTHER PUBLICATIONS

Sycle.net May 6, 2011 Press Release, http://web.sycle.net/wp-content/uploads/2011/09/Press-Release_Sycle_CounselEar-_050611.pdf, May 6, 2011.
Sycle.net Nov. 9, 2011 Press Release, http://web.sycle.net/wp-content/uploads/2011/09/PressRelease_NewFeatures_110911.pdf, Nov. 9, 2011.
What's new in Noah System 4.4, https://www.himsa.com/Portals/0/downloads/NOAH/Marketing/N44_Features_EN_2014.pdf, as early as Apr. 2014.
Noah 4 ride the wave new design, http://www.himsa.com/Portals/0/downloads/NOAH/Marketing/N4_Features_newdesign_en2.pdf, as early as Nov. 2010.
What is Noah System 4, http://www.himsa.com/Products/NoahSystem4Information/WhatisNoahSystem4/tabid/2382/language/en-US/Default.aspx, as early as Jan. 2015.
What is Noah System 4, http://www.himsa.com/Products/NoahSystem4Information/TheNoahStandard/tabid/74/language/en-US/Default.aspx, as early as 2014.
Noah 4 Audiogram Module, http://www.himsa.com/Portals/0/downloads/NOAH/Marketing/N4_AudMod_en-US_2014c.pdf, as early as Sep. 2014.
Module Certification Status, http://www.himsa.com/Products/NoahModules/CertifiedModules/tabid/2184/language/en-US/Default.aspx = various dates, earliest module Dec. 18, 2009. Most recent module Jun. 26, 2015.

* cited by examiner

METHODS AND SYSTEMS FOR ROUTING PATIENT INFORMATION TO A COMMUNICATION SERVICE PROVIDER AND TO A COMMUNICATION DEVICE FOR HEARING-IMPAIRED USERS

CROSS-REFERENCE TO RELATED APPLICATION

This application claims the benefit of U.S. Provisional Patent Application Ser. No. 62/127,227, filed Mar. 2, 2015, the disclosure of which is hereby incorporated herein in its entirety by this reference.

FIELD

The application relates generally to routing patient information in a communication network. More particularly, the disclosure relates to routing patient information of a hearing-impaired individual from office management system software or hearing diagnosis software of a hearing-care professional to a communication service provider or a communication device specifically configured for use by the hearing-impaired individual.

BACKGROUND

Hearing-impaired individuals may benefit from communication systems and devices configured to provide assistance in order to communicate with other individuals over a communication network. For example, assistive communication services (e.g., relay services) have been established to provide assistive services (e.g., text captions, sign language interpretive services, etc.) to the hearing-impaired user communicating with a communication device (e.g., caption phone, video phone, etc.) that is specifically configured to communicate with the communication service.

Such services and/or communication devices may be at least partially subsidized so that the services and communication devices may not be cost prohibitive for the hearing-impaired user. These subsidies may be provided by the government, which may pay for the communication devices as well as the per minute charges for using the assistive communication services. In some instances, hearing-impaired individuals may be required to meet minimum requirements to qualify for receiving the subsidy for the communication devices and services. For example, a hearing-impaired individual may, for example, be required to receive a certification from a hearing-care professional (e.g., audiologist, ear, nose, and throat doctor, family physician, hearing instrument specialist (HIS), etc.) certifying that the individual meets the standard for being considered hearing-impaired to qualify for the subsidy, or in some situations for participation in the services at all.

To obtain a certification of hearing loss, the hearing-impaired individual may visit with a hearing-care professional, who may complete a paper certification form to certify that the hearing-impaired individual has hearing loss. Typically, the hearing-care professional manually completes a paper copy of the certification form. The completed certification form may then be faxed, emailed, or mailed to a communication device provider by the hearing-care professional or the hearing-impaired individual. Unfortunately, completion and submission of the certification form requires the hearing-impaired individual to visit with a hearing-care professional, obtain the completed certification form from the hearing-care professional, and ensure that the signed certification form is transmitted to a communication service provider. The communication service provider then manually enters the data from the certification form into customer tracking software of the communication service provider. Because of the multiple steps and parties involved, the certification process can be time consuming, cumbersome, confusing, and undesirable and may hinder individuals with hearing impairment from completing the steps necessary for qualifying for the services.

BRIEF SUMMARY

Embodiments of the disclosure include an apparatus associated with a hearing-care professional, and configured to establish a communication channel with a device associated with a communication service provider for a hearing-impaired individual. The apparatus comprises communication elements configured to establish the communication channel with the communication service provider, and a processor operably coupled with the communication elements. The processor is configured to operate at least one of office management system software and hearing diagnosis software through which patient data is retrieved and transmitted over the communication channel to the device associated with the communication service provider.

Also disclosed is a method of establishing a communication channel between a computer device associated with a hearing-care professional and a device associated with a communication service provider. The method comprises generating a professional certification form with automatically populated patient data accessed through a software tool stored in the computer device, and transmitting the professional certification form from the computer device to the device associated with the communication service provider that provides interpretive services for the hearing-impaired user during a communication session with a far-end device.

Also disclosed is a method of establishing a communication channel between a computer device associated with a hearing-care professional and a communication device specifically configured for use by a hearing-impaired individual. The method comprises generating an audiogram related to the hearing-impaired individual through a software tool stored in the computer device, and transmitting the audiogram from the computer device to the communication device along with patient data retrieved through the software tool.

Also disclosed is an apparatus for establishing a communication channel with a computer device associated with a hearing-care professional and an assistive communication service configured to assist a hearing-impaired individual. The apparatus comprises communication elements configured to establish a communication channel with the computer device, and to receive an audiogram from the computer device, and a processor operably coupled with the communication elements and configured to automatically adjust configuration settings of the apparatus responsive to receiving the audiogram.

DETAILED DESCRIPTION

Figure 1:
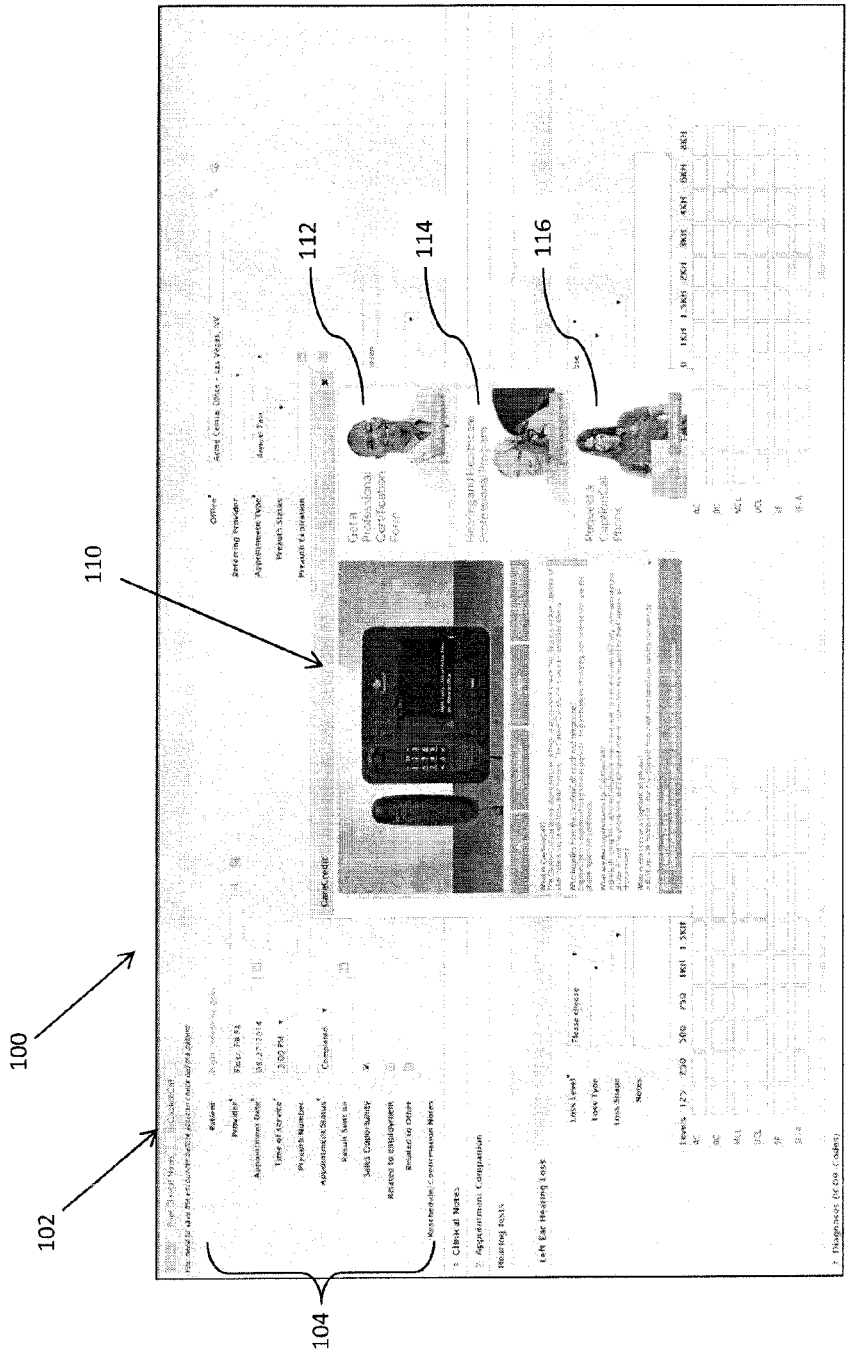
FIG. 1 is a user interface of office management system software configured for the office management of a hearing-care professional according to embodiments of the disclosure.

In the following detailed description, reference is made to the accompanying drawings which form a part hereof, and in which is illustrated specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions, rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the description may be represented by voltages, currents, electromagnetic waves, magnetic fields or particles, optical fields or particles, or any combination thereof. Some drawings may illustrate signals as a single signal for clarity of presentation and description. It should be understood by a person of ordinary skill in the art that the signal may represent a bus of signals, wherein the bus may have a variety of bit widths and the disclosure may be implemented on any number of data signals including a single data signal.

The various illustrative logical blocks, modules, circuits, and algorithm acts described in connection with embodiments disclosed herein may be implemented or performed with a general-purpose processor, a special-purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein.

A processor herein may be any processor, controller, microcontroller, or state machine suitable for carrying out processes of the disclosure. A processor may also be implemented as a combination of computing devices, such as a combination of a DSP and a microprocessor, a plurality of microprocessors, one or more microprocessors in conjunction with a DSP core, or any other such configuration. When configured according to embodiments of the disclosure, a special-purpose computer improves the function of a general-purpose computer because, absent the disclosure, the general-purpose computer would not be able to carry out the processes of the disclosure. The disclosure also provides meaningful limitations in one or more particular technical environments that go beyond an abstract idea. For example, embodiments of the disclosure provide improvements in the technical field of telecommunications, providing certification of hearing loss of a hearing-impaired individual to a communication service provider, communication devices connected to an assistive communication service, and other related technical fields. In particular, embodiments may improve the flow of data (e.g., a professional certification form) from a hearing-care professional to a communication service provider. Other embodiments include systems and methods for improving functionality of a communication device, and even transform the communication device by automatically adjusting the settings responsive to audiogram data received into the communication device directly from a hearing-care professional.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, interfacing with an operating system, etc. Furthermore, the methods disclosed herein may be implemented in hardware, software, or both. If implemented in software, the functions may be stored or transmitted as one or more instructions (e.g., software code) on a computer-readable medium. Computer-readable media includes both computer storage media and communication media including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

As used herein, a hearing-impaired user may be a person with diminished hearing capabilities. Some hearing-impaired users may have some level of hearing and/or speaking ability, while others may not have any such ability. Hearing-impaired users may need to be certified by a suitable hearing-care professional in order to access the communication system and/or receive a subsidy for their participation.

As used herein, "hearing-care professional" means and includes a professional qualified to test, diagnose, and/or treat hearing loss, such as an audiologist, an ear, nose, and throat (ENT) doctor, a family physician, a hearing instrument specialist (HIS), as well as technicians at hearing care clinics who may perform hearing tests, sell hearing aids, and program hearing aids for their patients. Because some features of the disclosure may be accessed by employees of the hearing-care professional, for purposes of this disclosure. a hearing-care professional may also include office staff who may operate under the direction of another hearing-care professional. Such individuals may include secretaries, receptionists, office managers, billing accountants, etc.

FIG. 1 illustrates a user interface 100 of office management system (OMS) software configured to provide office management services for a hearing-care professional. The OMS software may include a customer relationship management (CRM) tool. The OMS software may be configured to receive and store front-end information related to patients (i.e., hearing-impaired individuals) of the hearing-care professional. At times, the terms "patients" and "hearing-impaired individuals" may be used interchangeably.

The OMS software may be configured to receive inputs relating to a hearing-impaired individual including, for example, patient demographic information such as the individual's name, telephone number, address, email, etc. The OMS software may also be configured to provide calendaring services for the hearing-care professional office, scheduling, invoicing, and other services. In a typical hearing-care professional office, the OMS software may be used by office staff, receptionists, and the like. Some of the features of the OMS software may be included-within conventional software currently in use, such as Sycle Practice Management, commercially available from Sycle.net of San Francisco, Calif.

The user interface 100 may include a patient record area 104 configured to receive and/or display information relating to a particular patient. By way of non-limiting example, the patient record area 104 may be configured to receive and/or display information about the hearing-impaired individual such as a name, phone number, address, email address, the name of the hearing-care professional, a date, an authorization number, an appointment status, a reason for the hearing-impaired individual's appointment with the hearing-care professional, an area for the hearing-care professional to enter notes related to the hearing-impaired individual, an area to enter clinical notes, an area to enter hearing loss data of the hearing-impaired individual, etc. The patient record area 104 may include areas for inputting information relating to scheduling appointments, calendaring, invoicing, etc. The information from the patient record area 104 may be stored in an OMS database configured to manage patient information for the hearing-care professional.

The OMS software may further be configured to enable electronic completion of a certification form for the hearing-impaired individual, which is a feature not offered by conventional OMS software. As discussed above, for the hearing-impaired individual to qualify for certain communication devices (e.g., a text captioning phone, a video phone, etc.) or assistive communication services (e.g., text captioning services, video relay services, voice carry over, etc.), the hearing-impaired individual must show that they are qualified for such devices and services. Such a feature may enable the OMS software to have a channel of communication between the OMS software and the communication service provider for the hearing-impaired individual that currently does not exist in conventional OMS software that primarily has been focused on internal management of information. Transformation of conventional OMS software with this additional functionality may be provided by a module (e.g., applet) that integrates with the OMS software.

With continued reference to FIG. 1, the user interface 100 may include a communication service provider icon 102 (e.g., a button, tab, link, menu, etc.). Selecting the communication service provider icon 102 may cause the OMS software to open and display a communication service provider portal 110 configured to enable the hearing-care professional to communicate directly with the communication service provider through the OMS software. The communication service provider portal 110 may be opened within a window of the OMS software.

The communication service provider portal 110 may include one or more command icons 112, 114, 116 that may be selected (e.g., clicked) by the hearing-care professional to direct the OMS software to initiate different actions responsive to the command. By way of non-limiting example, the communication service provider portal 110 may display a professional certification form icon 112, a communication service provider information icon 114, and a request icon 116. Selecting the professional certification form icon 112 may generate a professional certification form with patient information retrieved from the OMS database automatically input into the appropriate fields. Selecting the communication service provider information icon 114 may provide the health-care service provider with additional information about the communication service provider. Selecting the request icon 116 may send a request for a communication device for demonstration purposes (a "demo" device), to request marketing and promotional materials, or other materials or devices. The communication service provider portal 110 may also display other information related to the communication device and/or service, such as a description of features, testimonials, frequently asked questions, etc. The communication service provider portal 110 may also be configured to contact a customer support representative to have live interaction to obtain additional information and/or assistance.

Figure 2:
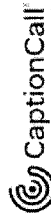
FIG. 2 is an exemplary professional certification form according to embodiments of the disclosure.

FIG. 2 is an exemplary professional certification form 200 that may be generated and displayed on the hearing-care professional's device responsive to receiving a command through the communication service provider portal 110 (e.g., such as by selecting the professional certification form icon 112).

The professional certification form 200 may include patient information 202 related to a hearing-impaired individual and hearing-care professional information 204 related to the hearing-care professional. The patient information 202 may include the hearing-impaired individual's name, street address, city, phone number, etc. The hearing-care professional information 204 may include the hearing-care professional's practice name, street address, email, etc. The patient information 202 may be automatically populated in the professional certification form 200 responsive to the hearing-care professional selecting the professional certification form icon 112. Similarly, the hearing-care professional information 204 may be automatically populated responsive to the hearing-care professional selecting the professional certification form icon 112. By way of non-limiting example, information about the hearing-care professional and information from the patient record area 104 may be stored in the hearing-care professional's OMS database. Responsive to the health-care professional selecting the professional certification form icon 112, the processor may retrieve the patient information 202 for a specific patient and the hearing-care professional information 204 from the OMS database, and automatically populate the fields in the patient information 202 and the hearing-care professional information 204 of the professional certification form 200. In addition, the professional certification form 200 may include a certification statement 206 for the hearing-care professional to certify that the hearing-impaired individual has hearing loss. The hearing-care professional may electronically sign the professional certification form 200 at an electronic signature block 208.

After the professional certification form 200 is completed by the hearing-care professional, the hearing-care professional may send the professional certification form 200 to a communication service provider over a network (e.g., IP network). In some embodiments, submission of the professional certification form 200 may automatically generate an electronic mail message with the professional certification form 200 as an attachment that is sent to the communication service provider. Other methods of transmission are also contemplated, including various forms of data transmission, messaging, etc. As a result, a communication path may be established between the OMS system of the hearing-care professional and the communication service provider for providing patient information to the communication service provider, and in particular a completed professional certification form 200.

In some embodiments, the professional certification form 200 may also include a machine-readable label that contains the information (e.g., patient information, provider information, etc.) from the professional certification form 200 therein. The machine-readable label may include, for example, a bar code, QR code, etc. The processor may generate the machine-readable label while generating the professional certification form 200 by retrieving the information used to populate the professional certification form 200, encoding the information into the machine-readable label, and including that label on the generated professional certification form 200.

The communication service provider may receive the patient information and/or professional certification form 200 from the hearing-care professional. In some embodiments, the professional certification form 200 may be received via email (e.g., as an attachment) or in another form. Some methods of transmission may result in an additional step of manual entry of the information into the database of the communication service provider, which may be simplified through the use of the machine-readable label.

In some situations, the patient information and/or professional certification form 200 may be associated with an existing customer of the communication service provider. As a result, the patient information and/or professional certification form 200 may be linked to the appropriate existing customer account maintained by the communication service provider. However, in some situations, the patient information and/or professional certification form 200 may be related to a prospective customer. Some prospective customers may already be known by the communication services provider, who may already have a record of the individual as an existing sales lead. As a result, the patient information and/or the professional certification form 200 may be linked to the appropriate existing entry for the existing sales lead. Some prospective customers may be completely unknown by the communication services providers. These individuals may be new sales leads, as they may not be aware that the communication service provider is capable of providing communication services and devices for their hearing impairment. As a result, the communication service provider may generate a new sales lead entry for a sales representative to contact these individuals. Such sales leads may be valuable, as the individuals are already known to have a hearing-impairment that meets the qualifications for participation in the service. As a result, the efforts of sales representatives can be even more targeted to the correct prospective customers. In addition, these sales leads have the additional benefit of already having received a valid and completed certification form. As a result, the additional burden to the hearing-impaired user may be removed in terms of it being a separate step to be completed.

Thus, transforming the OMS software to be additionally configured to generate and transmit the electronically signed professional certification form 200 may be beneficial to a hearing-impaired individual to be better informed about the services that may be available to the hearing-impaired individual. Hearing-care professionals may also benefit by providing their patients with additional beneficial services, which may also result in more patient satisfaction. The communication service provider may also benefit from receiving the electronically signed professional certification form 200 from the hearing-care professional as a lead generation tool to obtain information regarding potential customers who may already be certified to receive their services. The communication service provider may directly contact the hearing-impaired individual who is already qualified for services and devices offered by the communication device provider and inform the hearing-impaired individual of such services and devices.

Figure 3:
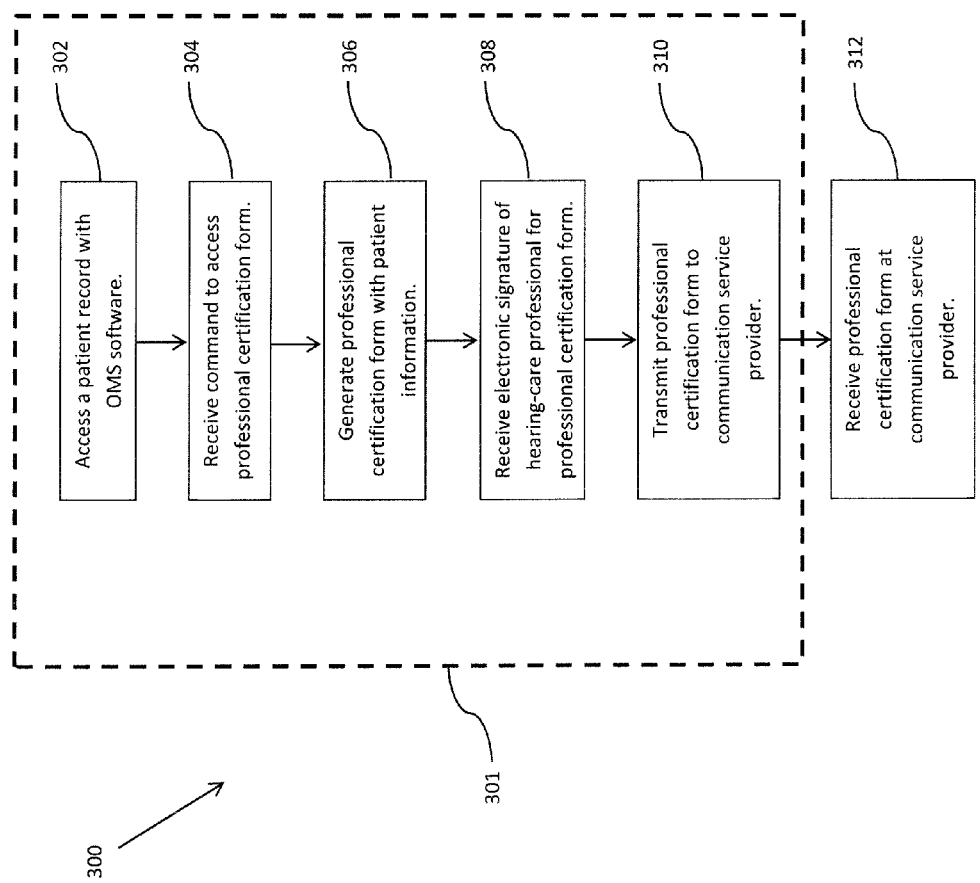
FIG. 3 is a flowchart illustrating a method of electronically transmitting a professional certification form for a hearing-impaired individual according to embodiments of the disclosure.

FIG. 3 is a flowchart 300 illustrating a method of electronically transmitting a professional certification form 200 for a hearing-impaired individual from a hearing-care professional to a communication service provider. Reference may also be made to FIG. 1 and FIG. 2 while describing the operations of the flowchart 300. Operations 302 through 310 may be performed on the computer of the hearing-care professional, whereas operation 312 may be performed by a server of the communication service provider. As indicated by box 301, operations 302-310 may also be performed within the OMS software of hearing-care professional.

At operation 302, a patient record including patient information of a hearing-impaired individual may be accessed by a processor through the OMS software. As discussed above, the OMS software may display the user interface 100, from which the hearing-care professional may access the patient information stored in the OMS patient database. The patient information may include demographic information (e.g., name, address, etc.) relating to the hearing-impaired individual, as well as some health information (e.g., hearing test results, etc.).

At operation 304, the processor may receive a command through the OMS software to access and generate the professional certification form 200. The hearing-care professional may enter a command to access the professional certification form 200 by selecting an icon located within the user interface 100. For example, the hearing-care professional may select the professional certification form icon 112 from the communication service provider portal 110, which may have been opened responsive to another command being received by the processor from a patient record.

At operation 306, the processor may generate the professional certification form 200 through the OMS software. The professional certification form 200 may be stored locally on the client side to be opened within the OMS software. The OMS software may generate the professional certification form 200 with the patient information 202 and the hearing-care professional information 204 automatically populated with information already stored within the OMS software (e.g., information from the patient record within the OMS database). The professional certification form 200 may include the electronic signature block 208 for the hearing-care professional's signature. The hearing-care professional may review the automatically populated information in the professional certification form 200 to verify completion and accuracy. If any of the automatically populated information is incorrect or incomplete, the hearing-care professional may fill in and complete the professional certification form 200. Thus, some information may be manually entered and/or edited by the hearing-care professional.

At operation 308, the professional certification form 200 may receive an electronic signature of the hearing-care professional at the electronic signature block 208. At operation 310, the OMS software may transmit the signed professional certification form 200 to a communication service provider, such as a provider of communication services configured to providing services for hearing-impaired individuals. The OMS software may transmit the professional certification form 200 responsive to receiving a command from the hearing-care professional to transmit the professional certification form 200. By way of non-limiting example, the hearing-care professional may select a "send" or a "submit" icon. Before the hearing-care professional may submit the professional certification form 200, the OMS software may also require that the hearing-care professional agree to certain legal requirements prior to actual transmission. For example, the hearing-care professional may be required to accept legal language, such as: "By sending Professional Certification Form to CaptionCall, I certify, under penalty of perjury, that I am a hearing-care or healthcare professional and am qualified to diagnose hearing loss. I have determined that the patient referenced in the form has been a hearing loss that makes it difficult to communicate effectively by telephone, and requires the use of captioned telephone service. The patient understands that the captioning service is provided by a live Communications Assistant and that this service is funded through a federal program for the hearing impaired."

Prior to actual transmission, the processor may verify the information on the professional certification form 200 for completeness. If the professional certification form 200 contains any fields that are incomplete, the OMS software may notify the hearing-care professional and prompt the hearing-care professional to complete the missing elements of the professional certification form 200. Once the professional certification form 200 is complete, the OMS software may transmit the professional certification form 200 to the communication service provider. The electronic signature may be secure because the OMS software from which the professional certification form 200 is originated may be limited to health care professionals such as hearing-care professionals.

At operation 314, the professional certification form 200 is received at the communication service provider. The professional certification form 200 may include a tracking code specific to the particular OMS from which the professional certification form 200 was originated. In some embodiments, the professional certification form 200 is received by the communication service provider as an attachment to an email or through other electronic data communication (e.g., .xml data, electronic fax, etc.). In some embodiments, the professional certification form 200 may be linked to a particular customer record in the customer database of the communication service provider if the associated hearing-impaired user is a current customer of the communication service provider. In some embodiments, the professional certification form 200 may be linked to a particular prospective customer record in a prospective customer database of the communication service provider if the associated hearing-impaired user is known as a prospective customer of the communication service provider. In some embodiments, a new prospective customer record may be generated and linked with the professional certification form 200 if the associated hearing-impaired user was previously unknown for a prospective customer of the communication service provider.

Figure 4:
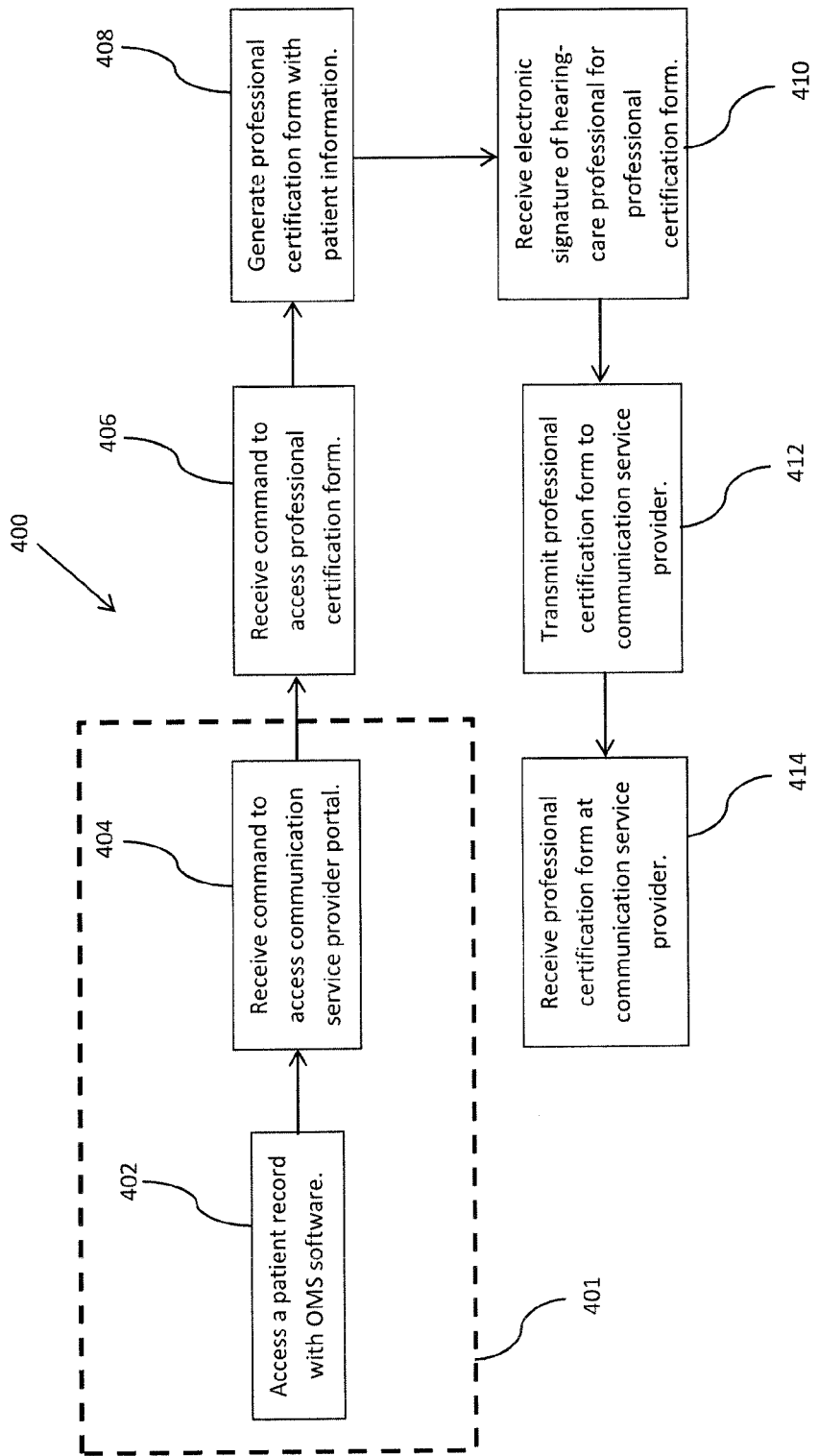
FIG. 4 is a flowchart illustrating another method of electronically transmitting a professional certification form for a hearing-impaired individual according to other embodiments of the disclosure.

FIG. 4 is a flowchart 400 illustrating another method of electronically transmitting a professional certification form 200 for a hearing-impaired individual from a hearing-care professional to a communication service provider. In general, operations 402 through 412 may be substantially similar to operations 302 through 312 of FIG. 3 in terms of a communication channel being established between the hearing-care professional and the communication service provider for generating and submitting a professional certification form 200 associated with a hearing-impaired individual through an integrated module accessing information from the OMS software. The primary difference between the method of FIG. 4 and the method of FIG. 3 is that the professional certification form may be built and controlled by the communication service provider rather than the OMS software controlling the professional certification form 200, as indicated by box 401. As a result of the communication service provider controlling the professional certification form 200, the communication service provider may make updates easier, as well as add additional marketing information, collateral ordering items and other desirable features.

By providing the hearing-care professional the electronic professional certification form 200, the hearing-impaired individual may obtain a completed professional certification form 200 more rapidly than would otherwise be available. The OMS software may be transformed to include functionality to generate the professional certification form 200, automatically populate the professional certification form 200, and receive the hearing-care professional's electronic signature on the professional certification form 200, and transmit the professional certification form 200 to the communication service provider. The hearing-care professional or the hearing-impaired individual may not be required to fax, email, mail, or otherwise deliver the professional certification form 200 to the communication service provider. Because the OMS software may check to ensure that all required fields of the professional certification form 200 are complete prior to sending the professional certification form 200 to the communication service provider, the communication service provider may receive more complete professional certification forms 200 than when the professional certification forms 200 are mailed, emailed, faxed, or otherwise delivered to the communication service provider. Accordingly, the professional certification form 200 may be sent to and received by the communication service provider while the hearing-impaired individual is at the office of the hearing-care professional. Thus, the communication service provider may receive information about the hearing-impaired individual who is already certified to receive a communication device. The communication service provider may contact the hearing-impaired individual to provide the hearing-impaired individual with a communication device and communication services without further action by the hearing-impaired individual.

In some embodiments, a module may be stored on the hearing-care provider's computer, which is configured to transform existing OMS software to enable generating a professional certification form 200, automatically populating the professional certification form 200, receiving an electronic signature and transmitting the professional certification form 200 to the communication service provider. Although the OMS software has been described above as being transformed from existing OMS software, it is contemplated that specialty OMS software may be developed to as a CRM tool that incorporates the functionality of transmitting a signed professional certification form 200 to the communication service provider. It is also contemplated that some embodiments may include a level of integration with the hearing-care professional's OMS database without having separate icons displayed on the OMS software user interface. In such an embodiment, a separate application program that may be opened in a separate window, but may access patient records to generate the professional certification form to be sent to the communication service provider.

Figure 5:
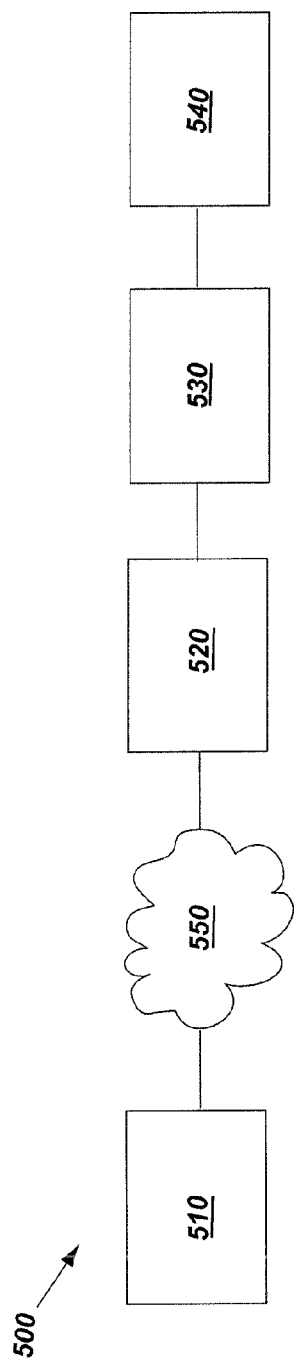
FIG. 5 is a simplified block diagram of a communication system configured to enable communication between a computer device associated with a hearing-care professional and devices associated with a communication service provider for the hearing-impaired.

FIG. 5 is a simplified block diagram of a communication system 500 configured to enable communication between a computer device 510 associated with a hearing-care professional and devices associated with a communication service provider for the hearing-impaired. The computer device 510 may transmit demographic data (e.g., patient data, provider data) along with the professional certification form 200 discussed above. In some embodiments, the information may be transmitted via email (e.g., as a pdf attachment) over a network 550 to an email server 520 (e.g., SMTP) associated with the communication service provider. The email server 520 may transmit the professional certification form 200 an inbox 530, from which the information may be stored in a database 540. In some embodiments, moving the information from the inbox 530 to the database 540 may be a manual process. The manual process may be simplified by reading the information into the system using a machine-readable label (e.g., bar code, QR code, etc.) containing the information from the professional certification form 200. In other embodiments, the process may be performed automatically. For example, the information from the attachment may be analyzed (e.g., optical character recognition) and automatically input into the database 540.

Figure 6:
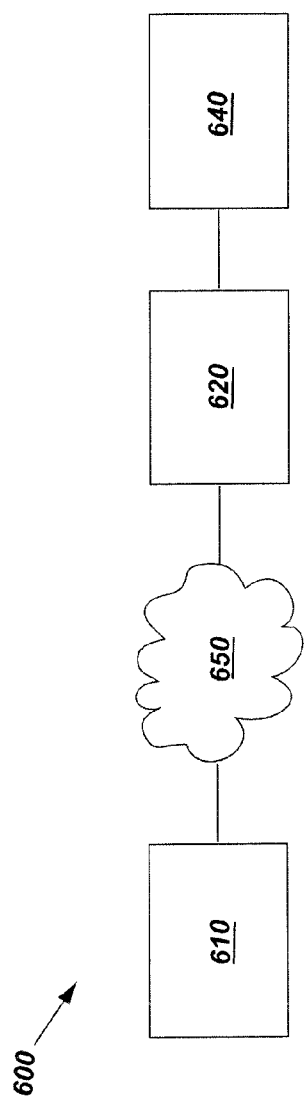
FIG. 6 is a simplified block diagram of a communication system configured to enable communication between a computer device associated with a hearing-care professional and devices associated with a communication service provider for the hearing-impaired.

FIG. 6 is a simplified block diagram of a communication system 600 configured to enable communication between a computer device 610 associated with a hearing-care professional and devices associated with a communication service provider for the hearing-impaired. The computer device 610 may transmit demographic data (e.g., patient data, provider data) along with the professional certification form 200 discussed above. In some embodiments, the information may be transmitted as packet data (e.g., xml, http, etc.) over a network 650 to an upload server 620 associated with the communication service provider. The upload server 620 may transmit data containing the professional certification form 200 to a database 640 for automatic storage.

In addition to OMS software, most hearing-care professionals may also utilize hearing diagnosis software for diagnosing hearing loss and performing hearing tests. As used herein, the term "hearing diagnosis software" means and includes software that may aid in diagnosing hearing loss and administering a patient test (e.g., speech tests, loudness scaling, etc.). The hearing diagnosis software may store and catalogue information relating to a patient test of a particular hearing-impaired individual (e.g., the hearing spectrum of the hearing-impaired individual). The hearing diagnosis software may also be configured to generate an audiogram that details the hearing-impaired individual's hearing capabilities over a range of frequencies, which the hearing-care professional may then use to diagnose and treat the hearing-impairment. The audiogram may be displayed as a graph that shows the audible threshold for standardized frequencies as measured by an audiometer. The Y axis represents intensity measured in decibels, and the X axis represents frequency measured in Hertz. The hearing diagnosis software may also be configured to program hearing aids and other related instruments. As a non-limiting example, such hearing diagnosis software may include NOAH, commercially available from the Hearing Instrument Manufacturer's Software Association (HIMSA) of Copenhagen, Denmark. Other examples of such hearing diagnosis software include manufacturer-specific software applications associated with an individual hearing aid manufacturer (e.g., Bernafon, Oticon, Phonak, Rexton, Siemens, Sonic Innovations, Starkey, Widex, etc.). Some hearing-diagnosis software (e.g., NOAH) may be configured to support integration with one or more different manufacturers.

The hearing diagnosis software may further be configured to enable the hearing-care professional's device to transmit an audiogram to a communication device associated with the hearing-impaired individual. The communication device may be a captioning communication device, a video phone, etc. that is configured to participate in an assisted call through an assistive communication service of a communication service provider. This communication channel between the hearing-care professional and a communication device is a feature not offered by conventional hearing-diagnosis software that primarily has been focused on internal management of information in the local diagnosis and treatment of hearing impairments, and in the programming of hearing aids. Transformation of conventional hearing diagnosis software with this additional functionality may be provided by a module (e.g., applet) that integrates with the hearing diagnosis software. In some embodiments, the module may be accessible through the user interface of the hearing diagnosis software. In some embodiments, the module may be accessible separately (e.g., through a separate desktop icon) without needing to open the entire hearing diagnosis software platform first. In each embodiment, the module may be configured to integrate with the hearing diagnosis software to the extent that information (e.g., patient information, audiograms, etc.) may be retrieved by the module and transmitted by the hearing-care professional's device to the hearing-impaired individual's communication device.

In some embodiments, the audiogram may be transmitted with a unique customer ID for the communication service provider to know to which communication device the audiogram should be routed. In unique customer ID may be an account number, an ID for the communication device itself (e.g., phone number), or other unique customer ID. The hearing-impaired user may provide that unique customer ID to the hearing-care professional so that the information may be transmitted with the audiogram. In some embodiments, the hearing-care professional may send patient information (e.g., name, address, birth date, etc.) as the unique customer ID along with the audiogram, which may be compared with customer information within the communication service provider's customer database in order to provide a match with a customer record to route the audiogram to the customer's communication device.

Figure 7:
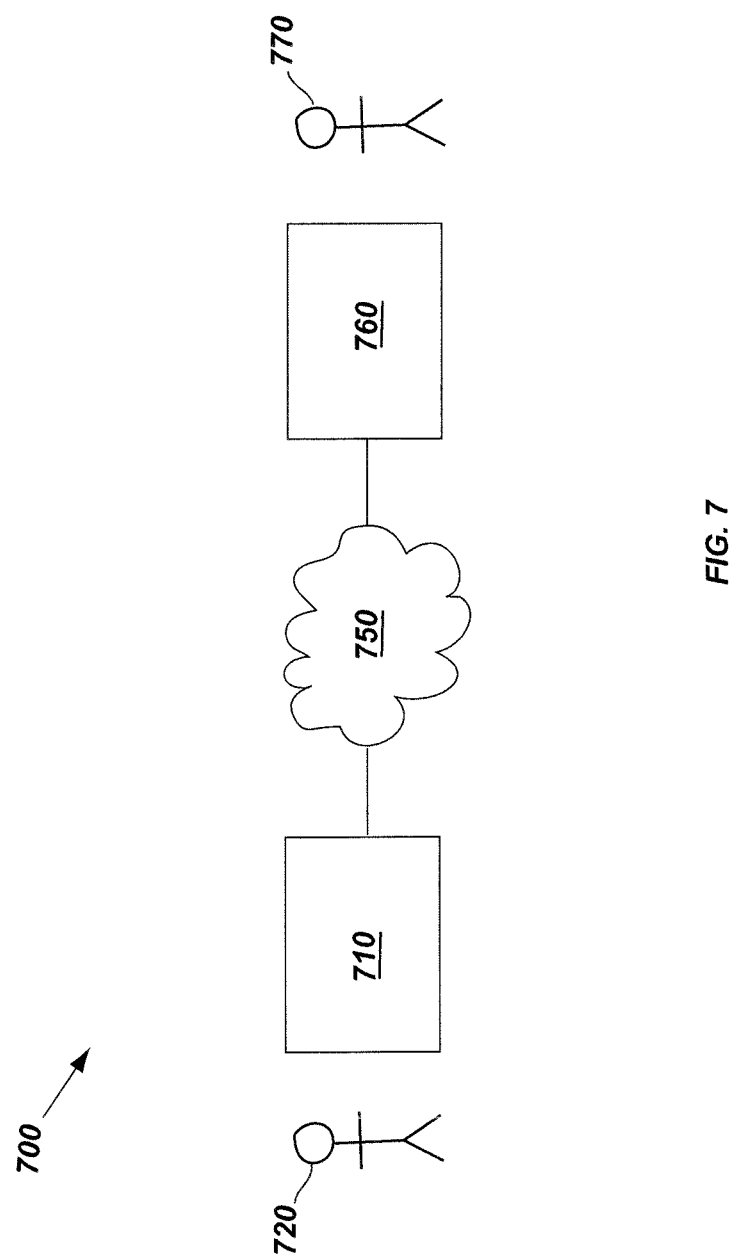
FIG. 7 is a simplified block diagram of a communication system configured to enable communication between a communication device associated with a hearing-impaired individual and a communication device associated with a hearing-care professional.

FIG. 7 is a simplified block diagram of a communication system 700 configured to facilitate transmission of information from a computer device 710 associated with a hearing-care professional 720 to a communication device 760 specifically configured for use by a hearing-impaired individual 770. The computer device 710 may be a computer configured to run hearing diagnosis software for the hearing-care professional to diagnose patients, treat patients, program hearing aids, and combinations thereof. The communication device 760 may be a device (e.g., caption phone, video phone, etc.) configured to assist hearing-impaired individuals communicate with others through an assistive communication service of a communication service provider. The computer device 710 may be coupled to the communication device 760 to facilitate communication therebetween via a network 750. Thus, a communication channel may be established between the computer device 710 of the hearing-care professional 720 and the communication device 760 of the hearing-impaired individual 770. Before accepting data from the hearing-care professional, the hearing-impaired individual 770 may be asked to accept terms and conditions through the specific communication device 760 to authorize the hearing-care professional 720 to transmit hearing data and messages, which may also impact the configuration settings of the communication device 760. In some embodiments, an additional authorization code may be required to confirm that the hearing-care professional 720 is the correct provider for that hearing-impaired individual 770. For example, the hearing-care professional 720 may have a unique provider code that the nearing-impaired individual 770 must provide in order to receive data.

As discussed above, the hearing-care professional 720 may perform hearing tests and provide other services to the hearing-impaired individual 770. One result of such testing may include an audiogram. The computer device 710 associated with the hearing-care professional 720 may be configured to transmit the audiogram to the communication device 760 over the network 750 (e.g., via xml, http, etc.). There may be an upload server within the network 750 configured to receive the audiogram and related information to determine the correct destination (e.g., based on a unique customer ID, patient information, etc.). The data may also be sent to a message queue prior to being received by the computer device 710.

The communication device 760 may be configured to receive information transmitted from the computer device 710. By way of non-limiting example, the communication device 760 may be configured to receive the audiogram information from the computer device 710. The communication device 760 may also be configured to automatically adjust its settings responsive to the audiogram and/or other information received from the computer device 710 of the hearing-care professional 720. Thus, the communication device 760 may automatically be transformed from a first state to a second state responsive to the receiving the audiogram data. The audiogram data may be discarded from the communication device 760 after settings are adjusted such that health records are not stored on the communication device 760.

For example, settings that may be adjusted include volume (e.g., overall volume, volume for frequency ranges, etc.), a volume override setting that keeps a customer's desired volume setting the same rather than resetting after each call, ring tone & pitch, a captioning font size, and other desirable settings. As an example, if the audiogram indicates that the hearing-impaired individual 770 exhibits hearing loss within a particular frequency of the hearing spectrum, the communication device 760 may increase the volume within the frequency ranges at which the hearing-impaired individual 770 exhibits hearing loss. Thus, the communication device 760 may incorporate the information from the audiogram to tailor the communication device 760 for the hearing-impaired individual's 770 particular hearing loss. This reconfiguration may occur while the hearing-impaired individual 770 is visiting with the hearing-care professional 720. As a result, the hearing-impaired individual 770 may not be required to reconfigure the communication device 760 manually or contact a technician to make adjustments to the communication device 760. As the hearing impairment of the hearing-impaired individual may change over time (e.g., due to age, lifestyle, environment, etc.), the hearing-impaired individual may consult with a hearing-care professional periodically to monitor, diagnose, and treat the individual's hearing impairment. As new audiograms are generated and then received by the communication device 760, the settings may automatically adjusted accordingly without requiring the process of manually configuring the communication device.

Additional information may also be transmitted from the hearing-care professional's device to the communication device of the hearing-impaired individual. For example, the hearing-care professional may be permitted to send other information that may be used to control settings of the hearing-impaired individual's communication device. For example, the hearing-care professional 720 may be permitted to use her expertise to control settings that may not be adjusted by the audiogram data or that may override the standard adjustments for the audiogram data. For example, the hearing-care professional may set an overall threshold volume, above which the hearing-care professional 720 may determine that it would be damaging or otherwise undesirable for the hearing-impaired individual 770 to be exposed to. Responsive to receiving this information, the communication device 760 may be configured such that the output volume of the communication device 760 does not exceed the threshold volume.

In addition, the communication channel between the hearing-care professional's device and the hearing-impaired user's communication device may be used to transmit additional information therebetween. For example, the computer device 710 may be configured to transmit additional information, such as appointment reminders, a reminder to schedule an appointment, and other messages from the hearing-care professional 720. The communication device 760 may be configured to visually display the messages received from the computer device 710. In some embodiments, the communication channel may be used to transmit information from the communication device 760 of the hearing-impaired individual 770 to the computer device 710 of the hearing-care professional 720. For example, the hearing-impaired individual 770 may initiate and/or respond to messages through the communication device 760 (e.g., ask questions, confirm appointments, schedule appointments, verify information, etc.).

Figure 8:
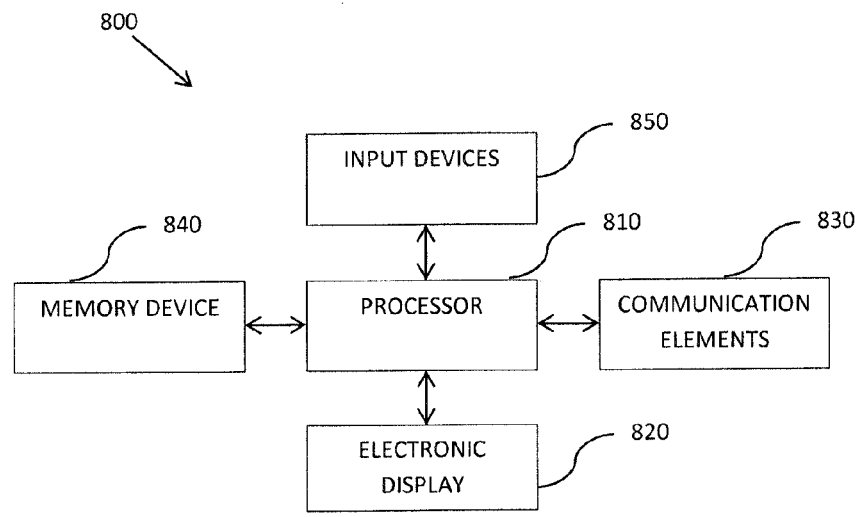
FIG. 8 is a simplified schematic block diagram of a computer device that is associated with the hearing-care professional according to an embodiment of the disclosure.

FIG. 8 is a simplified schematic block diagram of a computer device 800 that is associated with the hearing-care professional according to an embodiment of the disclosure. For example, the computer device 800 may be configured as one of the computer devices 510, 610, 710 of FIGS. 5, 6, 7. In particular, the computer device 800 may be configured to operate OMS software, hearing diagnosis software, and associated modules described herein. While embodiments are described herein refer to a certification form being generated from an OMS software, and audiograms being generated from hearing diagnosis software, it is contemplated that any combination of functions may be implemented. For example, modules may be implemented to integrate with OMS software to send audiograms if such data is available to the OMS software. Likewise, modules may be implemented to integrate with hearing diagnosis software to generate and send professional certification forms if such data is available to the hearing diagnosis software. In addition, another contemplated embodiment may include a single software platform that has the functionality described herein as the OMS software and the hearing diagnosis software.

The computer device 800 may include a processor 810 operably coupled with an electronic display 820, communication elements 830, a memory device 840, and input devices 850. The processor 810 may coordinate the communication between the various devices as well as execute instructions stored in computer-readable media of the memory device 840. The processor 810 may be configured to execute a wide variety of operating systems and applications including the computing instructions. The memory device 840 may be used to hold computing instructions, data, and other information for performing a wide variety of tasks including performing embodiments disclosed herein. By way of example and not limitation, the memory device 250 may include Synchronous Random Access Memory (SRAM), Dynamic RAM (DRAM), Read-Only Memory (ROM), Flash memory, and the like. The memory device 840 may include volatile and non-volatile memory storage for the computer device 800.

The communication elements 830 may be configured for communicating with other devices or communication networks. As non-limiting examples, the communication elements 830 may include elements for communicating on wired and wireless communication media, such as for example, serial ports, parallel ports, Ethernet connections, universal serial bus (USB) connections IEEE 1394 ("firewire") connections, Bluetooth wireless connections, 802.1 a/b/g/n type wireless connections, and other suitable communication interfaces and protocols. The input devices 850 may include a keyboard, a touchscreen, a remote control, a mouse, other input devices, or combinations thereof. For embodiments where audiograms may be generated and other tests performed, the input devices 850 may include instruments such as audiometers.

The communication elements 830 may also be configured to establish communication channels between at least one of a communication service provider and the communication devices thereof. As discussed above, the computer device may be configured to generate and send professional certification forms to a communication service provider and/or to send audiograms and other data to a communication device of a hearing-impaired user. This information may be transmitted through the communication elements 830.

Figure 9:
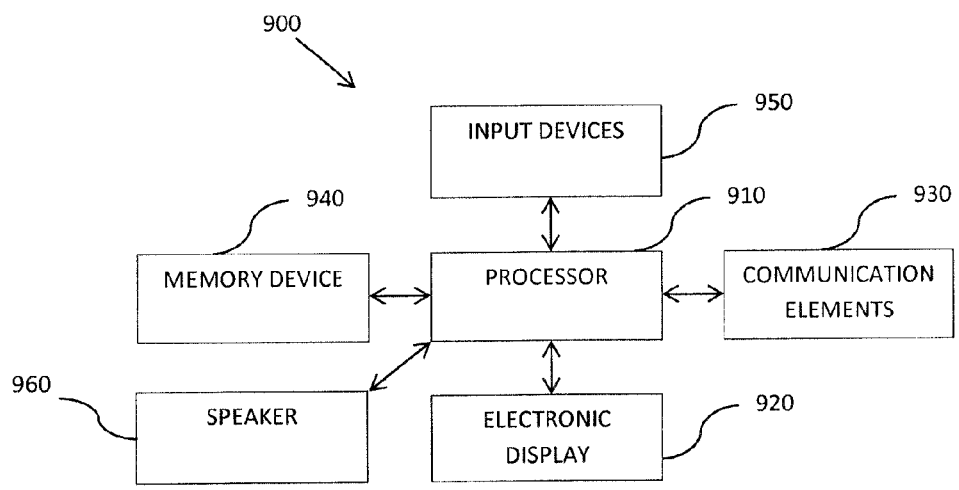
FIG. 9 is a simplified schematic block diagram of a communication device associated with a hearing-impaired user according to an embodiment of the disclosure.

FIG. 9 is a simplified schematic block diagram of a communication device 900 specifically configured for use by a hearing-impaired user according to an embodiment of the disclosure. For example, the communication device 900 may be configured as the communication device 760 of FIG. 7. In particular, the communication device 900 may be configured to establish communication sessions with other communication devices and an assistive communication service configured to assist the hearing-impaired user. The communication device 900 may be a caption phone, video phone, etc., which may be implemented as a standalone device, or as implemented on another device (e.g., tablet computer, laptop computer, smart phone, etc.). As discussed above, the communication device 900 may also be configured to establish a communication channel between a computer device of a hearing-care professional. In particular, the communication device 900 may receive audiogram data directly from the hearing-care professional, and automatically adjust settings in response thereto. The communication device 900 may also send and/or receive additional data and messages with the computer device of the hearing-care professional as discussed above.

The communication device 900 may include a processor 910 operably coupled with an electronic display 920, communication elements 930, a memory device 940, input devices 950, and a speaker 960. The processor 910 may coordinate the communication between the various devices as well as execute instructions stored in computer-readable media of the memory device 940. The processor 910 may be configured to execute a wide variety of operating systems and applications including the computing instructions. The memory device 940 may be used to hold computing instructions, data, and other information for performing a wide variety of tasks including performing embodiments disclosed herein. By way of example and not limitation, the memory device 940 may include Synchronous Random Access Memory (SRAM), Dynamic RAM (DRAM), Read-Only Memory (ROM), Flash memory, and the like. The memory device 940 may include volatile and non-volatile memory storage for the communication device 900.

The communication elements 930 may be configured for communicating with other devices or communication networks, including other communication devices, an assistive communication service, as well as devices associated with a hearing-care professional. As non-limiting examples, the communication elements 930 may include elements for communicating on wired and wireless communication media, such as for example, serial ports, parallel ports, Ethernet connections, universal serial bus (USB) connections IEEE 1394 ("firewire") connections, Bluetooth wireless connections, 802.1 a/b/g/n type wireless connections, and other suitable communication interfaces and protocols. The input devices 950 may include a numeric keypad, a keyboard, a touchscreen, a remote control, a mouse, other input devices, or combinations thereof.

Figure 10:
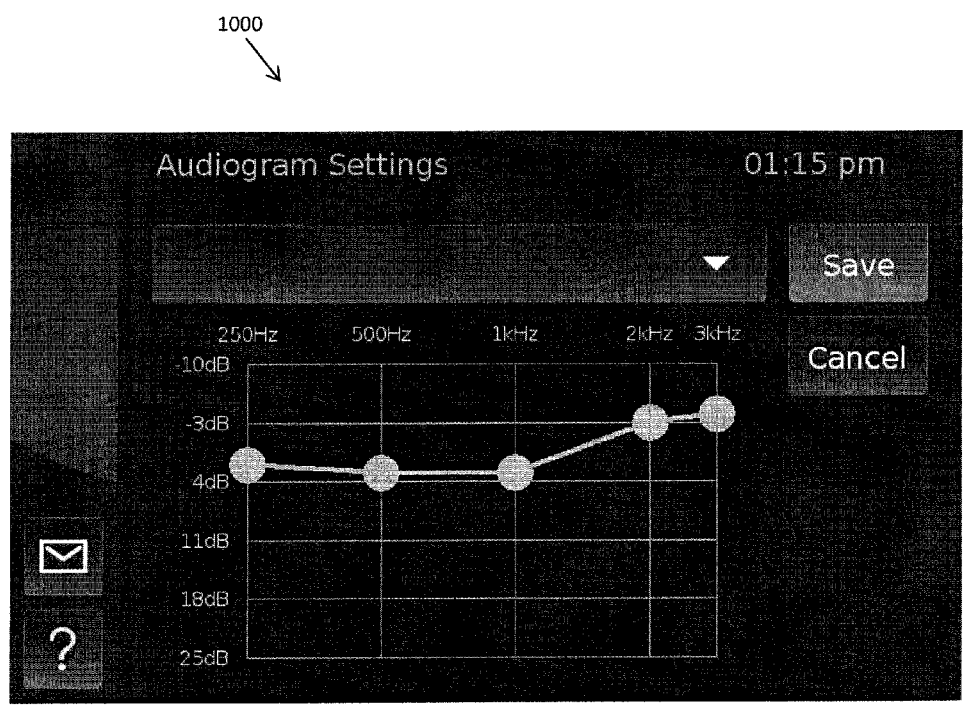
FIG. 10 is a screenshot of an audiogram setting interface of a communication device according to an embodiment of the disclosure.

FIG. 10 is a screenshot of an audiogram setting interface 1000 of a communication device according to an embodiment of the disclosure. The audiogram setting interface 1000 includes a graph displaying the audiogram settings that may be stored by communication device. The audiogram settings may be set according to the audiogram received from the hearing-care professional. As shown in FIG. 10, there may be a number of data points used to generate the audiogram settings. While five data points are shown in FIG. 10, more or fewer data points may be included within the audiogram. In some embodiments, the audiogram setting interface may permit the user to manually override and adjust the audiogram settings. Changing these audiogram settings may cause additional configuration settings (e.g., volume, ring tone, pitch, etc.) to be adjusted.

Figure 11:
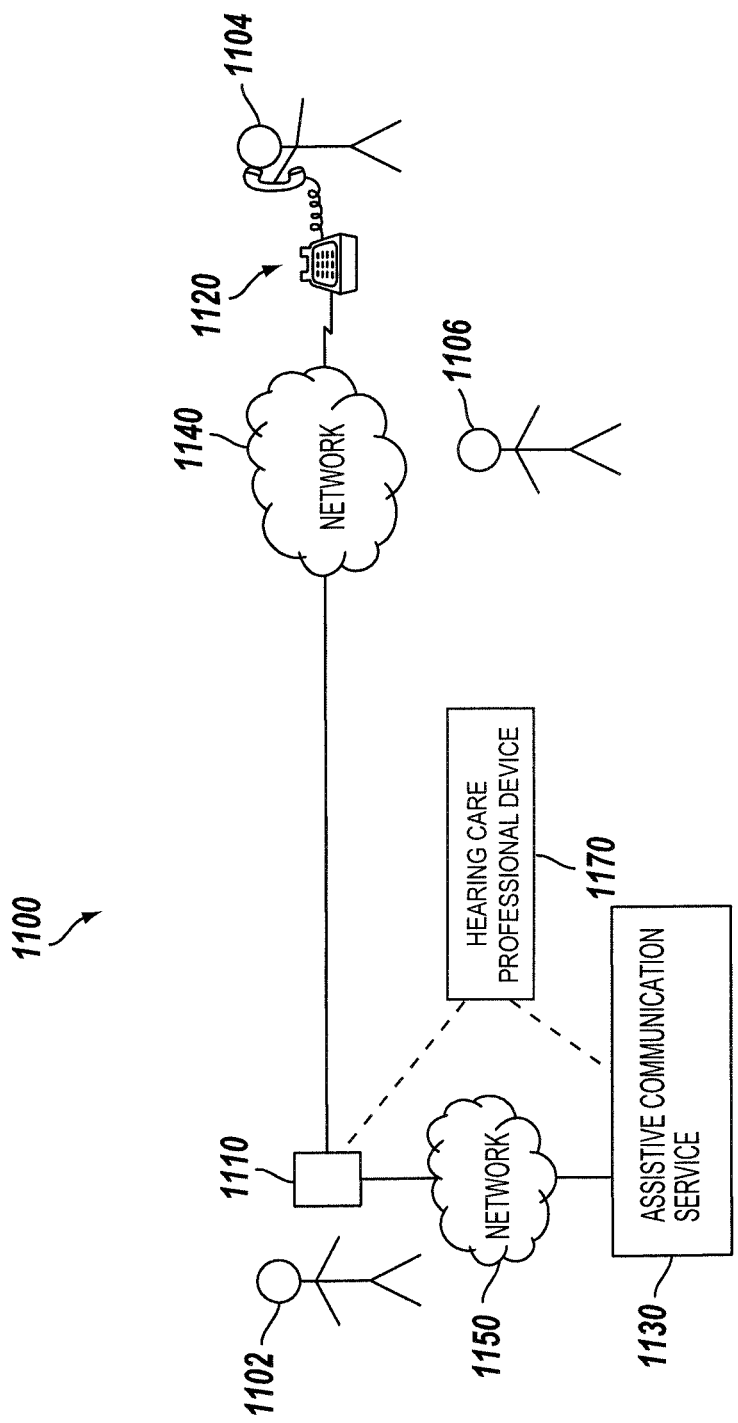
FIG. 11 illustrates a communication system configured to facilitate a communication session between a hearing-impaired user and a hearing-capable user according to an embodiment of the disclosure.

FIG. 11 illustrates a communication system 1100 configured to facilitate a communication session between a hearing-impaired user 1102 and a hearing-capable user 1104 according to an embodiment of the disclosure. The communication system 1100 may include a first communication device 1110, a second communication device 1120, and an assistive communication service 1130. The communication system 1100 may also include a hearing-care professional device 1170 that is associated with a hearing-care professional 1106. The hearing-care professional device 1170 may be configured as discussed above to retrieve patient data and transmit the patient data to the assistive communication service 1130 and/or the first communication device 1110. For example, the hearing-care professional device 1170 may have stored thereon OMS software and/or hearing diagnosis software that is further configured to retrieve patient data to generate a professional certification form and/or audiogram data as discussed above.

The first communication device 1110 and the second communication device 1120 may be coupled together to facilitate communication therebetween via a first network 1140. The first communication device 1110 and the assistive communication service 1130 may be coupled together to facilitate communication therebetween via a second network 1150. For example only, the first network 1140 and the second network 1150 may each be implemented according to the standards and bandwidth requirements of a communication network (e.g., Public Switch Telephone Network (PSTN), cellular network, Voice Over Internet Protocol (VOIP) networks, etc.). The use of the terms "network" or "communication network" as used herein contemplates networks that are compatible and configured to provide communications using analog and/or digital standards unless specifically stated otherwise. In some embodiments, the first network 140 and the second network 150 may be the same network (e.g., both connections may be Internet-based connections). Thus, discussion of the first network 1140 and the second network 1150 separately may be for convenience of discussing a particular connection between two or more devices. Of course, in some embodiments, the first network 1140 and the second network 1150 may be different networks. For example, the first communication device 1110 and the second communication device 1120 may communicate via a PSTN network connection, while the first communication device 1110 and the second communication device 1120 may communicate via an internet connection. Other variations and combinations of networks are also contemplated.

The first communication device 1110 may include a device that is configured to assist the hearing-impaired user 1102 in communicating with another individual (e.g., hearing-capable user 1104 or another hearing-impaired user). In some embodiments, the first communication device 1110 may include a captioned telephone, a telephone enabled for text enhanced telephony, or any other suitable communication device configured to receive and display a text caption of at least a portion of the conversation. Thus, the hearing-impaired user 1102 may be able to read a caption of the words spoken by the hearing-capable user 1104 to supplement the audio generated by the first communication device 1110 from the voice signal received by the first communication device 1110. As a result, the hearing-impaired user 1102 may have an improved experience in understanding the conversation. Such an embodiment may be useful for people whose hearing has been damaged or decreased over time (e.g., the elderly); such that they can still speak but have diminished hearing that makes it difficult to communicate. In some embodiments, the first communication device 1110 may include a communication device (e.g., video telephone) configured to receive and display video on an electronic display on the first communication device 1110. In addition, the first communication device 1110 may include a camera configured to capture and transmit a video signal to the assistive communication service 1130 and/or the second communication device 1120. As a result, the hearing-impaired user 1102 may be able to use visual communication (e.g., sign language) to communicate with others. Such an embodiment may be useful for people whose hearing has been damaged or decreased over time, but who may not be able to verbally communicate well and/or have such damaged hearing that they cannot hear.

The second communication device 1120 may comprise a conventional voice telephone (e.g., landline phone, cellular phone, smart phone, VoIP phone, etc.). As such, the hearing-capable user 1104 may interact in a conventional manner with the second communication device 1120. In some embodiments, the second communication device 1120 may be configured similarly as the first communication device (e.g., captioned phone, video phone, etc.). As a result, the second communication device 1120 may likewise be operated by a hearing-impaired user. Thus, although facilitating communication between the hearing-impaired user 1102 and the hearing-capable user 1104 is shown in FIG. 11, such a situation is shown only as an example. Other embodiments include both the first communication device 1110 and the second communication device 1120 coupled to the assistive communication service 1130 to facilitate the interpretive services for each respective hearing-impaired user.

The assistive communication service 1130 may be configured to provide interpretive services (e.g., captioning, video) to the hearing-impaired user 1102. More specifically, a human "call assistant" within assistive communication service 1130 may be employed to facilitate a communication session between a hearing-impaired user 1102 and a hearing-capable user 1104. As discussed above, in some embodiments the assistive communication service 1130 may be configured to provide text captions of at least a portion of the conversation. In such an embodiment, the call assistant may listen to the voice signal received and re-voice the portion of the conversation into a microphone so that voice recognition software may generate the text transcription that is transmitted to the first communication device 1110. In some embodiments, the assistive communication service 1130 may be configured to provide sign language interpretive services. In such an embodiment, the call assistant may communicate with the hearing-impaired user 1102 over a video connection (e.g., via sign language), and then the call assistant may then communicate with the hearing-capable user over a voice connection. Thus, the assistive communication service 1130 may include one or more of an internet protocol captioned telephone service (IPCTS), captioned telephone service (CTS), video relay service (VRS), or other telecommunications relay services (TRS).

FIG. 11 shows a configuration where the first communication device 1110 acts as a router for the voice signal from the second communication device 1120 to the assistive communication service 1130. In such an embodiment, the voice signal of the hearing-capable user 1104 may be transmitted from the second communication device 1120 to the first communication device 1110. The voice signal of the hearing-capable user 1104 may then be transmitted from the first communication device 1110 to the assistive communication service 1130 for the text transcription to be generated in a text captioning embodiment. The text transcription may then be transmitted from the assistive communication service 1130 to the first communication device 1110 to be displayed as a text caption for the hearing-impaired user to read during the conversation. The call assistant may also monitor the text transcription that is generated and transmitted to the first communication device 1110 to identify any errors that may have been generated by the voice recognition software. In some embodiments the assistive communication service 1130 may be configured to receive the voice signal from the second communication device 1120 and route the voice signal to the first communication device 1110. In some embodiments, another device may receive the voice signal from the second communication device 1120 and split the voice signal to route to both the first communication device 1110 and the assistive communication service 1130.

In addition, although FIG. 11 shows only two communication devices 1110, 1120, the communication system 1100 may include more communication devices. It is contemplated that the communication system 1100 may facilitate communication between any number and combinations of hearing-impaired users and hearing-capable users. For example, in some embodiments two or more communication devices may be connected for facilitating communication between a hearing-impaired user and other hearing-impaired users and/or hearing-capable users.

While certain illustrative embodiments have been described in connection with the figures, those of ordinary skill in the art will recognize and appreciate that embodiments encompassed by the disclosure are not limited to those embodiments explicitly shown and described herein. Rather, many additions, deletions, and modifications to the embodiments described herein may be made without departing from the scope of embodiments encompassed by the disclosure, such as those hereinafter claimed, including legal equivalents. In addition, features from one disclosed embodiment may be combined with features of another disclosed embodiment while still being encompassed within the scope of embodiments encompassed by the disclosure as contemplated by the inventors.

What is claimed is:

1. A method comprising:
   obtaining, at a remote captioning service, an audiogram of a patient and patient data of the patient from a hearing diagnosis software tool of a hearing-care professional computer device associated with a hearing-care professional;
   selecting, by the remote captioning service, a communication device that corresponds to the patient by comparing the patient data with customer data of the remote captioning service;
   directing, from the remote captioning service, the audiogram to the communication device;
   automatically adjusting call configuration settings of the communication device responsive to receiving the audiogram from the remote captioning service, wherein the call configuration settings are configured to adjust levels of audio output by the communication device during communication sessions with other devices, the call configuration settings selected from the group consisting of: an overall volume, a volume over one or more specific frequency ranges, a ring tone and pitch, and combinations thereof;
   establishing, by the communication device, a communication session with a far-end communication device;
   obtaining, at the communication device, text data from the remote captioning service, the text data including transcription of audio from the far-end communication device during the communication session; and
   applying the adjusted call configuration settings during the communication session.

2. The method of claim 1, further comprising transmitting additional messaging data from the hearing-care professional computer device to the communication device.

3. A communication device comprising:
   an electronic display;
   communication elements;
   a processor operably coupled with the communication elements and the electronic display, the processor configured to:
      establish, via the communication elements, communication sessions with far-end communication devices;
      receive text captions, via the communication elements, from the remote captioning service during the communication sessions;
      receive, via the communication elements from the remote captioning service, audio settings data from an audiogram, the audiogram originating from a computer device associated with a hearing-care professional; and
      automatically adjust call configuration settings of the communication device responsive to receiving the audio settings data, wherein the call configuration settings are configured to adjust levels of audio output by the communication device during communication sessions with the far-end communications devices and the call configuration settings are selected from the group consisting of: an overall volume, a volume over one or more specific frequency ranges, a ring tone and pitch, and combinations thereof.

4. A method comprising:
   obtaining, at a remote captioning service, a first audiogram of a patient and first patient data of the patient from a hearing diagnosis software tool of a hearing-care professional computer device associated with a hearing-care professional;
   generating, at the remote captioning service, a customer record using the first patient data;
   directing, from the remote captioning service, first audio settings from the first audiogram to a communication device associated with the customer record;
   automatically adjusting call configuration settings of the communication device responsive to receiving the first audio settings from the remote captioning service, wherein the call configuration settings are configured to adjust levels of audio output by the communication device during communication sessions with other devices, the call configuration settings selected from the group consisting of: an overall volume, a volume over one or more specific frequency ranges, a ring tone and pitch, and combinations thereof;

establishing, by the communication device, a first communication session with a far-end communication device;

obtaining, at the communication device, text data from the remote captioning service, the text data including transcription of audio from the far-end communication device during the first communication session;

applying the adjusted call configuration settings during the first communication session;

obtaining, at the remote captioning service, a second audiogram of the patient and second patient data of the patient from the hearing diagnosis software tool of the hearing-care professional computer device associated with the hearing-care professional;

comparing the second patient data with customer data of the remote captioning service to identify the customer record;

selecting, by the remote captioning service, the communication device that corresponds to the customer record;

in response to selecting the communication device, directing, from the remote captioning service, second audio settings from the second audiogram to the selected communication device;

automatically readjusting the call configuration settings of the communication device responsive to receiving the second audio settings from the remote captioning service; and applying the readjusted call configuration settings during a second communication session.

* * * * *